United States Patent
Jia

(10) Patent No.: US 7,226,960 B2
(45) Date of Patent: Jun. 5, 2007

(54) SELF-ETCHING PRIMER ADHESIVE AND METHOD OF USE THEREFOR

(75) Inventor: Weitao Jia, Wallingford, CT (US)

(73) Assignee: Pentron Clinical Technologies, LLC, Wallingford, CT (US)

( * ) Notice: Subject to any disclaimer, the term of this patent is extended or adjusted under 35 U.S.C. 154(b) by 353 days.

(21) Appl. No.: 10/442,476

(22) Filed: May 21, 2003

(65) Prior Publication Data

US 2003/0207960 A1     Nov. 6, 2003

Related U.S. Application Data

(63) Continuation-in-part of application No. 09/852,938, filed on May 10, 2001, now abandoned.

(51) Int. Cl.
*A61K 6/083* (2006.01)
*A61C 5/00* (2006.01)

(52) U.S. Cl. ............... 523/115; 523/118; 523/120; 433/228.1

(58) Field of Classification Search ............... 523/115, 523/118, 120
See application file for complete search history.

(56) References Cited

U.S. PATENT DOCUMENTS

| | | |
|---|---|---|
| 4,593,054 A | 6/1986 | Asmussen et al. |
| 4,719,149 A | 1/1988 | Aasen et al. |
| 4,802,950 A | 2/1989 | Croll |
| 4,880,660 A | 11/1989 | Aasen et al. |
| 5,061,183 A | 10/1991 | Nicholson |
| 5,256,065 A | 10/1993 | Nicholson |
| 5,264,513 A | 11/1993 | Ikemura et al. |
| 5,294,691 A * | 3/1994 | Ahmed et al. ............... 526/287 |
| 5,525,648 A | 6/1996 | Aasen et al. |
| 5,756,560 A | 5/1998 | Antonucci et al. |
| 5,925,690 A * | 7/1999 | Fuchigami et al. ......... 523/118 |
| 5,954,996 A | 9/1999 | Discko |
| 6,004,390 A | 12/1999 | Pflug et al. |
| 6,071,983 A | 6/2000 | Yamamoto et al. |
| 6,147,137 A | 11/2000 | Jia |
| 6,217,644 B1 | 4/2001 | Matsunae et al. |
| 6,312,667 B1 | 11/2001 | Trom et al. |
| 6,355,704 B1 | 3/2002 | Nakatsuka et al. |
| 6,572,693 B1 * | 6/2003 | Wu et al. ..................... 106/35 |
| 6,759,449 B2 | 7/2004 | Kimura et al. |
| 6,939,900 B2 | 9/2005 | Ario et al. |
| 2003/0055124 A1 | 3/2003 | Klee et al. |
| 2004/0156795 A1 | 8/2004 | Nemoto et al. |
| 2004/0229973 A1 | 11/2004 | Sang et al. |
| 2004/0235981 A1 | 11/2004 | Qian |
| 2005/0014861 A1 | 1/2005 | Qian |
| 2005/0049326 A1 | 3/2005 | Park et al. |

* cited by examiner

*Primary Examiner*—Tae H Yoon
(74) *Attorney, Agent, or Firm*—Cantor Colburn LLP

(57) ABSTRACT

A self-etching, priming dental adhesive composition comprises an olefinically unsaturated monomer having an —$SO_3$ functionality; a copolymerizable multi-functional (meth)acrylate adhesive; and a curing system. The self-etching, priming dental adhesive may further comprise a copolymerizable adhesion promoter containing an acid functionality, the adhesion promoter being different from the olefinically unsaturated monomer having an —$SO_3$ functionality and the copolymerizable multi-functional (meth)acrylate adhesive, and a solvent system in an amount effective to dissolve the adhesive and/or the adhesion promoter. The adhesive composition provides even further advantages over the art, as all etching, priming, and application of an adhesive can be performed in one step.

20 Claims, No Drawings

SELF-ETCHING PRIMER ADHESIVE AND METHOD OF USE THEREFOR

CROSS REFERENCE TO RELATED APPLICATIONS

This application is a continuation-in-part of U.S. application Ser. No. 09/852,938, filed May 10, 2001, now abandoned which is incorporated by reference herein in its entirety.

TECHNICAL FIELD

The present invention relates to compositions for preparing the surface of a tooth prior to repair or restoration, in particular to compositions and methods for simultaneously etching and priming the surface of a tooth prior to the application of dental adhesives and/or filling materials, and more in particular to compositions and methods for simultaneously etching, priming and adhering.

BRIEF DESCRIPTION OF THE RELATED ART

Methods and compositions for improving the adhesion of resins to hard tissue, i.e., dentin or enamel, is an ongoing goal in the dental arts. Improved adhesion leads to longer lasting restorations and reduced tooth sensitivity. Numerous methods for preparing teeth for the application of a dental restorative material (such as a sealant, filling material, cementation of indirect dental restorations or the like) have accordingly been developed, including acid etch and priming steps. Unfortunately, such steps have increased operating time and complexity.

Acid etchants are commonly thought to remove a smear layer and demineralize the tooth surfaces so as to promote effective mechanical bonding of the restorative material. However, the use of an etchant has a disadvantage, in that it must be washed off after application, requiring the time-consuming procedure of application, washing and drying. A further disadvantage of etchants is the perception that use of strong etchants can increase dental sensitivity in some patients.

In addition to acid etch procedures, adhesive strength is also improved by use of a primer. Primers are generally surface-active compounds that exhibit both an affinity for dentin and adhesive resin systems and participate in the polymerization process, thereby promoting adhesion between the primarily hydrophilic dentin and the predominantly hydrophobic polymeric adhesives or monomers from which they are formed. Primers are applied to dentin in solution form, commonly used solvents including acetone, ethanol, water, and various mixed solvent systems. A widely used primer is N-phenylglycine (NPG), which, in addition to its surface-active properties, also functions as a co-initiator or activator during interfacial polymerization. While effective for promoting bonding, primers are often applied using an additional step.

There accordingly remains a need in the art for improved compositions which improve adhesion to a tooth surface, which do not increase tooth sensitivity, and yet which can be applied in a fewer number of steps.

SUMMARY OF THE INVENTION

The above-described drawbacks and disadvantages are alleviated by a self-etching primer composition comprising an olefinically unsaturated monomer having a terminal —$SO_3$ functionality, selected from the group consisting of 2-acrylamido-2-methyl-propanesulfonic acid (AMPS), its esters, salts, and combinations thereof, 2-sulfoethyl methacrylate (SEM), its esters, salts, and combinations thereof, and 3-sulfopropylmethacrylate (SPM), its esters, salts, and combinations comprising at least one of the foregoing monomers. The monomer is present in quantities effective to provide etching and priming, generally in the range from about 0.1 to about 50 weight percent of the total composition. In a particularly advantageous feature, the composition increases the adhesiveness of the tooth structure without the need for washing the composition from the tooth surface. This composition can accordingly be provided as a single component material for ease of application and storage.

In another embodiment, a self-etching, priming dental adhesive composition comprises an olefinically unsaturated monomer having an —$SO_3$ functionality; a copolymerizable multi-functional (meth)acrylate adhesive; and a curing system. The self-etching, priming dental adhesive may further comprise a copolymerizable adhesion promoter containing an acid functionality, the adhesion promoter being different from the olefinically unsaturated monomer having an —$SO_3$ functionality and the copolymerizable multi-functional (meth)acrylate adhesive, and a solvent system in an amount effective to dissolve the adhesive and/or the adhesion promoter. The one-part adhesive composition provides even further advantages over the art, as all etching, priming, and application of an adhesive can be performed in one step.

In accordance with the method of use, one of the above-described compositions is physically contacted with the tooth structure, and then at least partially dried prior to application of an adhesive or restorative composition.

DETAILED DESCRIPTION OF THE PREFERRED EMBODIMENTS

In one embodiment, the inventor hereof has unexpectedly discovered monomers having both olefinic unsaturation and terminal —$SO_3$ groups, such as an —$SO_3H$ group, are effective to simultaneously etch and prime a tooth to receive a dental restoration, and can be used as self-etching priming compositions. Examples of monomers having both olefinic unsaturation and terminal —$SO_3$ groups, such as an —$SO_3H$ group, include 2-acrylamido-2-methyl-propanesulfonic acid (AMPS), 2-sulfoethyl methacrylate (SEM) and its derivatives, 2-sulfopropyl (meth)acrylate, 4-sulfobutyl (meth)acrylate, 3-sulfobutyl (meth)acrylate, 3-bromo-2-sulfopropyl (meth)acrylate, 3-methoxy-1-sulfo-propyl (meth)acrylate, 1,1-dimethyl-2-sulfoethyl (meth)acrylamide, 3-sulfopropyl methacrylate (SPM), and active derivatives (esters and salts) of the foregoing. A combination comprising at least one of the foregoing acids, esters, or salts may also be used. Examples of derivatives include sulfonic acid salts of AMPS, SEM, and SPM, and hydrolytically active esters of AMPS, SEM, and SPM. AMPS compounds are available from Lubrizol Corporation, Wickliffe, Ohio SEM and SPM compounds are available from Polyscience, Inc., Pa.

A self-etching priming composition in accordance with the present invention accordingly comprises a solution of a one or more of AMPS, SEM, SPM, and/or their derivatives. Suitable salt counter ions include, without limitation, alkali and alkaline earth metals. Suitable ester moieties include without limitation lower alkyl groups, for example $C_1$–$C_{12}$ groups such as methyl, ethyl, propyl, isopropyl, and the like, as well as aromatic groups such as benzyl.

Preferably, the —SO₃ terminated monomers are present in the self-etching, priming composition in amounts from about 0.1 to about 50 weight percent, more preferably about 0.1 to about 20 weight percent, and most preferably from about 1 to about 10 weight percent of the total composition. The particular amounts are selected to provide effective etching and priming (enhanced adhesion).

The etchant/primer adhesive composition may further comprise additional, optional components for enhancing the priming, cleaning or conditioning effect of the composition. Such components include chemicals containing polymerizable double bonds such as those of methacrylic acid, ester, or similar groups; additional acids with good or limited solubility in water; surfactants; and dyes such as methylene blue, and the like. More specifically, examples of useful priming components include 2-hydroxyethylmethacrylate, glyceryl methacrylate, hydroxypropylmethacrylates, itaconic acid, ethyleneglycolmethacrylate, maleic acid, 2-(methacryloyloxy)ethyl phosphate, and the like. The composition may also optionally contain a hydrophilic resin or monomer, such as for example, hydroxyethyl methacrylate (HEMA). These optional components are generally present in amounts in the range of up to about 50 weight percent.

In another embodiment, the inventor has further discovered a self-etching, priming adhesive composition that will, in one operation, etch the tooth surface, i.e., remove dentin smear and etch/dissolve calcium minerals from the surface of the tooth structure, prime the tooth surface; and form a resin coating on the tooth structure that will polymerize to form a reliable bond with the tooth structure and a dental restorative material. The composition can accordingly be used without intermediate washing, second priming, or adhesion steps. The composition comprises an olefinically unsaturated monomer having an —SO₃ functionality as described above; a copolymerizable multi-functional (meth) acrylate adhesive; and a curing system. The self-etching, priming dental adhesive may further comprise a copolymerizable adhesion promoter containing an acid functionality, the adhesion promoter being different from the olefinically unsaturated monomer having an —SO₃ functionality and the copolymerizable multi-functional (meth)acrylate adhesive, and a solvent system in an amount effective to dissolve the adhesive and/or the adhesion promoter.

The copolymerizable multi-functional (meth)acrylate adhesive may be monomeric, oligomeric, or polymeric, and has at least two (meth)acrylate functionalities that are copolymerizable with the olefinically unsaturated monomer having an —SO₃ functionality. As used herein, the term "(meth) acrylate" is intended to encompass both acrylate and methacrylate groups. Non-limiting examples of preferred copolymerizable multi-functional (meth)acrylate adhesives include difunctional hydrophilic (water dispersible) ethoxylated Bisphenol A di(meth)acrylates, preferably having about 10 to about 30 ethoxy groups, ethoxylated tetrabromo bisphenol A diacrylates, preferably having about 10 to about 30 ethoxy groups, polyethylene glycol di(meth)acrylates, preferably having about 200 to 600 ethylene glycol groups, metallic di(meth)acrylates, highly propoxylated glyceryl tri (meth)acrylates, preferably having about 10 to about 30 propoxy groups, trifunctional monomers of pentaerythritol tri(meth)acrylate, tetrafunctional monomers of pentaerythritol tetra(meth)acrylate, pentafunctional monomers of pentaerythritol penta(meth)acrylate, pentaerythritol dimethacrylate(PEDM), dipentaerythritol penta(meth)acrylate (DPEPA), trimethylolpropane tri(meth)acrylate (TMPTMA), ethoxylated trimethylolpropane tri(meth)acrylates, preferably having about 10 to about 30 ethoxy groups, di-trimethylolpropane tetraacrylate, tris(2-hydroxyethyl) isocyanurate, glycerol di(meth)acrylate, triethylene glycol dimethacrylate (TEGDMA), the diglycidyl (meth)acrylate adduct of Bisphenol A (Bis-GMA), urethane dimethacrylate (UDMA), or a combination having of one or more of the foregoing adhesives. Adhesive compositions comprising a mixture of a monomeric compound together with an oligomeric and/or a polymeric compound are preferred. The relative weight ratio of monomeric to oligomeric and/or polymeric adhesive is 1:100 to 100:1, preferably 1:50 to 50:1, more preferably 1:25 to 25:1. These adhesives are useful in preparing combined etchant/bonding compositions because they can be applied in one or a relatively few number of coats and achieve a uniform thin coating of the dental substrate, while providing high bonding strengths between the dental substrate and the restorative material or dental component.

The self-etching, priming adhesive composition may further optionally comprise a co-polymerizable adhesion promoter for example an olefinically unsaturated monomer resin containing an acid functionality. The adhesion promoter may function as a primer, may be monomeric, oligomeric, or polymeric, and may have carboxyl and/or phosphoryl groups, together with at least one copolymerizable ethylidenyl, acrylate, or methacrylate group. Preferred copolymerizable adhesion promoters include but are not limited to N-tolyglycine-N-glycerol methacrylate, pyromellitic acid dimethacrylate (PMDM), dipentaerythritol-pentaacrylate-phosphoric acid ester (PENTA), bis(2-ethylhexyl)hydrogen phosphate, 2(methacryloyloxy)-ethyl phosphate, a butane tetracarboxylic acid-bis-hydroxyethylmethacrylate (TCB resin), methacrylic acid, maleic acid, p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid ("4-MET") and an anhydride thereof ("4-META"), 4(2-hydroxy-3-methacryloyloxy) butyltrimellitic acid and an anhydride thereof, 2,3-bis(3,4-dicarboxybenzoyloxy) propyl methacrylate, methacryloyloxytyrosine, N-methacryloyloxyphenylalanine, methacryloyl-p-aminobenzoic acid, an adduct of 2-hydroxyethyl methacrylate with pyromellitic dianhydride (PMDM), an adduct of 2-hydroxyethyl methacrylate with 3,3',4,4'-benzophenonetetracarboxylic dianhydride (BTDA) or 3,3',4,4'-biphenyltetracarboxylic dianhydride, BPDM, which is the reaction product of an aromatic dianhydride with an excess of 2-HEMA (2-hydroxyethyl methacrylate), the reaction product of 2-HEMA with ethylene glycol bistrimellitate dianhydride (EDMT), the reaction product of 3,3', 4,4'-diphenylsulfone tetracarboxylic dianhydride and 2-HEMA (DSDM), the adduct of pyromellitic dianhydride with glycerol dimethacrylate (PMGDM), or a combination comprising at least one of the foregoing adhesion promoters.

In the self-etching, priming adhesive composition, the olefinically unsaturated monomer having an —SO₃ functionality is present in amounts of about 0.1 to about 50 weight percent, more preferably about 0.1 to about 20 weight percent, and most preferably about 1 to about 10 weight percent of the total composition. The particular amounts are selected to provide effective etching and priming (enhanced adhesion). The copolymerizable multi-functional (meth)acrylate adhesive comprises about 0.1 to about 50 weight percent, more preferably about 0.1 to about 20 weight percent, and most preferably about 1 to about 10 weight percent of the total composition.

When used, the co-polymerizable adhesion promoter comprises about 0.1 to about 50 weight percent, more preferably about 0.1 to about 20 weight percent, and most preferably about 1 to about 10 weight percent of the total composition. Solvents as describe below, when present, comprise about 0.1 to about 99 weight percent, more preferably about 20 to about 90 weight percent, and most preferably about 30 to about 70 weight percent of the total composition The self-etching, priming adhesive composition further comprises a curing system, i.e., polymerization initiators, optionally together with polymerization accelerators, for example tertiary amines, to facilitate curing upon mixing or exposure to actinic light. The compositions may be provided as one- or two-part compositions, the two-part compositions containing an initiator in one part and an accelerator in another part, the two parts being combined prior to use. Preferred photoinitiators are those that do not affect the shelf life of the one-part composition, for example phosphine oxides. It has been unexpectedly found that elimination of polymerization accelerators from the curing system improves shelf life one-part compositions, particularly when phosphine oxide photoinitiators are used. Suitable commercially available phosphine oxide photoinitiators include, but are not limited to, the LUCIRIN™ series from BASF Corp. such as LUCIRIN™ TPO (L-TPO) and LUCIRIN™ 8809. Other phosphine oxide photoinitiators may be selected from the DAROCUR™ or IRGACURE™ series from Ciba-Geigy Corp. Examples include DAROCUR™ TPO, DAROCUR™ 4265, IRGACURE™ 1800, and the like. The total amount of curing system is typically about 0.1 to about 5 weight percent, preferably about 1 to about 3 weight percent.

The self-etching, priming adhesive composition may optionally comprise fillers. Examples of suitable filling materials include but are not limited to, silica, quartz, strontium silicate, strontium borosilicate, lithium silicate, lithium alumina silicate, amorphous silica, ammoniated or deammoniated calcium phosphate, tricalcium phosphate alumina, zirconia, tin oxide, titania and combinations comprising at least one of the foregoing fillers. Organic-inorganic fillers such as polyhedral oligomeric silsesquioxanes (POSS™, available from Hybrid Plastics), zirconium methacrylate and zirconium dimethacrylate (CXZR050 and CXZR051, available from Gelest, Inc.) can also be used. Suitable high refractive index filler materials such as high refractive index silica glass fillers; calcium silicate based fillers such as apatites, hydroxyapatites or modified hydroxyapatite compositions may also be used. Alternatively, inert, non-toxic radiopaque materials such as bismuth oxide ($Bi_2O_3$), zirconium oxide, barium sulfate, and bismuth subcarbonate in micro- or nano scaled sizes may be used.

Suitable fillers have particle sizes of about 0.01 to about 5.0 micrometers, and may further comprise bound or unbound silicate colloids of about 0.001 to about 0.2 micrometers. These additional fillers may also be treated with a silane-coupling agent. Commercially available silane treated fumed silica based on Aerosil A200 can be obtained from Degussa Corp under the names of Aerosil R711 and R7200.

The amount of total filler composition can vary from about 0.1 to about 50%, preferably up to about 20% by weight, based on the total weight of the adhesive composition. The amount used is determined by the requirements of the particular application.

Any of the present compositions may further include optional additives such as flavoring agents, disinfectants, color indicators, a fluoride source, and the like. Suitable fluoride sources that are compatible with the —$SO_3$ terminated monomers include, for example, sodium fluoride, stannous fluoride, sodium monofluorophosphate, calcium fluorophosphate, and the like. When present, fluoride-releasing compounds are used in quantities of up to about 2% by weight of the total composition.

Any of the present compositions may further include a solvent system. Such a solvent system may include water and/or a polar solvent that is partially or totally soluble in water. For dental applications, a suitable solvent system is one that completely wets and diffuses into the conditioned surface of enamel, and particularly dentin, in a clinically acceptable period of time (on the order of about 15 to about 180 seconds). Preferred organic solvents include low molecular weight ketones, such as acetone and methyl ethyl ketone, which are readily soluble in water over a wide concentration range, or a low molecular weight alcohol, such as ethanol or propanol. Other solvents include polar aprotic liquids such as dimethylformamide, dimethylacetamide, and dimethylsulfoxide. Water, ethanol, acetone, or a mixed solvent system of water and ethanol or acetone is preferred. In such a solvent system, the amount, by volume, of ethanol or acetone may be about 5 to about 50% acetone, with the remainder being water. A preferred solvent in the self-etching, priming adhesive composition is effective to dissolve the components of the composition, in particular the copolymerizable multi-functional (meth)acrylate adhesive. Thus, water miscible hydrophilic monomers such as 2-HEMA, or combinations of miscible hydrophilic monomers and the previously described solvents may be used.

The solvent serves the purpose of assuring that the components of the compositions contact the exposed dentin surfaces so that the components can function successfully. Thus, the solvent system must appropriately reduce the viscosity of the etchant/primer compound as well as provide a suitable surface tension such that the composition may penetrate the smallest cracks, fissures or pores in the dentin surface to assure suitable contact of the polymerized adhesive component with the dentin. In some instances, to provide the appropriate surface tension, a surfactant may be employed. In most instances, as when the etchant/primer compound is combined with an monomer system, it is preferred that the solvent system used to dissolve the etchant/primer compound also be miscible with the solvent system employed to dissolve the adhesive monomer system and/or be capable of dissolving the adhesive monomer system itself.

The amount of solvent used is 100 weight percent less the total amount of other components, preferably 30 to 99 weight percent, more preferably 40 to 95 weight percent of the total composition. Distilled or deionized water is preferred, as it does not contain impurities potentially harmful to the adhesive properties of the solution. When volatile solvents such as ethanol or acetone are used in the composition, the amount of water may be decreased to as low as 2 percent.

The present compositions may be applied directly to the prepared tooth surface. The compositions may be dispensed from a conventional push syringe or squeeze bottle, or applied with a brush. Preferably, after a specified time ranging from 5 to 120 seconds, preferably 10 to 60 seconds, the tooth surface is lightly dried. Washing is not required.

After applying the primer/etchant composition, a polymerizable dental adhesive system may be applied, dried, and optionally cured, followed by application and curing of a dental restorative material. The dental adhesive bonds to the tooth without the need for the tooth to be washed. The term 'dental adhesive' and the like as used herein can apply to a wide range of materials that can affect a bond to both conditioned enamel and dentin. At a minimum, the dental adhesive contains a polymerizable resin component or components necessary to effect the initiation and acceleration of polymerization by visible or actinic light or by chemical means, and a polymerizable monomer or monomers containing anionic functionality such as a phosphate or carboxylic (—COOH) acid function. Examples of monomers include TEGDMA, 2-HEMA, Bis-GMA, PUDMA, TMPTMA, and the like. This dental adhesive may be in the form of a self-priming adhesive that further contains a volatile solvent such as acetone, ethanol, and mixtures thereof. Water may also be used as a solvent. The dental adhesive may comprise a one-component material, or may alternatively have two components. The second component of the dental adhesive may contain initiators and/or accelerators, to facilitate chemical curing alone or combined with curing upon exposure to actinic light to provide a dual-cure mode of polymerization. Examples of substances that facilitate self-curing of dental adhesives include for example, BPO, DHEPT, and aromatic sulfinic acid salts. One useful dental adhesive includes Bond One™ (available from Pentron Corp.). Preferred dental adhesives are cured by exposure to light, preferably visible light.

Alternatively, as described above, a copolymerizable dental adhesive system may be included in the etchant/primer adhesive composition, combining the application of the etchant/primer and the application of the dental adhesive into a single step. In this embodiment, after applying the self-etching, priming adhesive composition to the site to be restored, the composition may be dried and optionally cured, followed by application and curing of a dental restorative material. Two or more applications of the composition may be used. Suitable dental restoratives are those conventional in the art.

Useful dental restorative materials or cements that may be used together with the compositions include amalgam and non-amalgam dental restoratives. Examples of useful non-amalgam materials include compomer restorative, composite resin restorative, glass ionomer-resin restorative, glass ionomer-resin luting cement, resin cement and resin dental sealant.

The composition when applied to a tooth enhances the adhesiveness of the tooth without the need for washing or a second application step. The multi-step bonding protocols typical of current commercial adhesive systems generally tend to be a source of material waste and unreasonable technique sensitivity. The present all-in-one adhesive compositions not only reduce the number of steps normally involved in preparing a substrate surface and applying the dental restorative materials, but less waste and improved restorative or sealant results are obtained.

Furthermore, although conventional aggressive etchants are effective in cleaning the surface of dentin for improved wetting, they can also weaken the underlying sound dentin by excessive demineralization and disruption of collagen fibrils. These types of etchants typically require an aqueous rinse step to remove residual acid and soluble by-products. Also, the depth of demineralized, altered dentin resulting from the use of aggressive etchants may exceed the depth to which an adhesive resin can penetrate the dentin, resulting in a weakened, partially reinforced hybrid dentin zone, and thereby become vulnerable to failure. In contrast, the present compositions are milder and may be used as single step composition without subsequent rinsing since they are also effective in the presence of water and/or aqueous solvents. Accordingly, while an aqueous rinse step, such as the type used with multi-step systems to remove residual acid and soluble by-products, may be used, it is unnecessary to employ such a rinse step. Another advantage of the mildness of the present compositions is that sensitivity for the patient at the site of the restoration is reduced.

The following non-limiting examples illustrate the invention.

EXAMPLES

In Examples 1–9, the etchant/primer adhesive compositions set forth in Table 1 below were applied onto the tooth surface for 30 seconds and then blot dried with a tissue paper (Kimwipes EX-L, Kimberly-Clark, Ga.). There was no water rinse procedure after the etchant/primer adhesive composition was applied. The light curing time for the Bond-1, Bond-1 C&B and Lockjaw adhesives was 10 seconds. Bond-1 and Bond-1 C&B are visible light curable dental adhesives from Pentron Corp., Wallingford, Conn. Lockjaw adhesive is a partially filled light cured adhesive in gel form from Doctors Research Group, Inc., Conn.

If the etchant/primer adhesive composition was used alone, as in Examples 4 and 7, a light cure initiator was added to the etchant/primer adhesive composition, and light curing was conducted for approximately 20 seconds. The dentin and enamel bonding strength test methods are the same as those described in the U.S. Pat. No. 6,147,137, which is hereby incorporated by reference, except that the 37% phosphoric acid etch has been replaced by the self-etch primer/adhesive formulations in the examples.

Example 9 is a comparative example showing the use of 37% phosphoric acid as an etching material. The phosphoric acid solution was applied to the surface for 20 seconds and blot dried. Prime & Bond NT™ was thereafter applied. The bond strength was very low in comparison to the etchant compositions of the invention.

In the Tables below, all components are by weight relative to the total composition. The etchant/primer adhesive compositions were all aqueous solutions unless otherwise specified.

TABLE 1

| | Self-Etch Compositions | | | |
|---|---|---|---|---|
| Example No. | Etchant/primer Adhesive | Bonding Adhesive | Bond Strength to dentin (S.D.), MPa | Bond Strength to enamel (S.D.), MPa |
| 1 | 2.2% AMPS | Bond-1* (Lot No. 33790) | 21.2 (3.0) | — |

TABLE 1-continued

Self-Etch Compositions

| Example No. | Etchant/primer Adhesive | Bonding Adhesive | Bond Strength to dentin (S.D.), MPa | Bond Strength to enamel (S.D.), MPa |
|---|---|---|---|---|
| 2 | 2.2% AMPS | Lockjaw adhesive ** | — | 25.4 (6.2) |
| 3 | 5% AMPS | Bond-1 C&B* (Lot No. 33088) | 15.1 (5.7) | — |
| 4 | 5% AMPS 20% HEMA 1% TMPTMA 2% UDMA 20% ethanol | None | 11.4 (4.1) | — |
| 5 | 10% AMPS 10% Ethanol | Bond-1 C&B (Lot No. 33088) | 16.9 (2.1) | 12.4 (5.5) |
| 6 | 10% SEM | Bond-1 (Lot No. 27716) | 14.4 (2.7) | — |
| 7 | 10% SEM 10% HEMA 1% TMPTMA 3% BISGMA 20% ethanol | None | 12.3 (3.2) | — |
| 8 | 10% SEM 10% HEMA | Bond-1 (Lot No. 27716) | 15.8 (4.7) | — |
| Example 9 (Comparative) | 37% $H_3PO_4$ applied for 20 seconds and blot dried | Prime&Bond NT (Lot No. 000605) | 5 (2.0) | — |

AMPS: $H_2C=CHC(O)NHC(CH_3)_2CH_2SO_3H$
SEM: $H_2C=C(CH_3)CO_2(CH_2)_2SO_3H$
SPM: $H_2C=C(CH_3)CO_2(CH_2)_3SO_3H$

Self-etching, priming adhesive compositions are illustrated in Examples 10–22, as follows. Each test group consists of six tooth samples. Each tooth was mounted with a cold-cured acrylic in a cylinder form leaving the crown portion exposed. Occlusal dentin was then exposed by cutting off the enamel portion of the tooth crown using a slow speed diamond wheel saw, Model 650 (South Bay Technologies, Inc.). The exposed dentin was then subjected to silicon carbide (SiC) abrasive paper through 600 grits. After the dentin surface was cleaned and water rinsed, it was lightly dried with a jet of air for two to three seconds to remove apparent water on the surface. Then the formulas as set out in Table 2 were applied onto the tooth surface with a disposable brush tip in a number of coats indicated. After letting the formulas on the tooth surface to stand for about twenty seconds, a gentle flow of air was applied to the surface for about thirty seconds to remove any remaining solvent. The tooth surface was then exposed to visible light cure for a time using an Optilux 400 light-curing unit (Demetron/Kerr) at a radiation intensity of about 600 mw/cm².

An Ultradent dentin bonding device/jig (Ultradent, UT) was used for mounting the tooth bonding sample and for making a composite cylinder on top of the cured adhesive surface. A Simile™ A 3.5 shade composite (Pentron Corp.) was used for the composite button build-up, the composite button having a diameter of 2.38 mm and about 2 mm thickness. The composite was then light cured for forty seconds from the top only.

The tooth bonding sample was then removed from the Ultradent jig and placed in tap water for twenty-four hours at 37° C. before subjecting the sample to the bonding test. The bonding test was done in push-shear mold using the Ultradent device in conjunction with an ATS machine under a crosshead speed of 0.02 inch/minute. The load at which the composite button was broken/fractured from the tooth was recorded. The bonding strength was calculated using the maximum load divided by the composite cylinder's surface area and expressed in Mega Pascal (Mpa). The standard deviation (S.D.) was then calculated based on each group of samples.

The compositions and results for the bonding test are shown in Table 2.

TABLE 2

| Component | Sample No. | | | | | | | | | | | | |
|---|---|---|---|---|---|---|---|---|---|---|---|---|---|
| | 10* | 11 | 12 | 13 | 14 | 15 | 16 | 17 | 18 | 19 | 20 | 21* | 22** |
| AMPS | 2.2 | | | 3.0 | 3.0 | 2.4 | 2.4 | 2.4 | 2.6 | 2.5 | 2.5 | | 2.3 |
| SEM | | 14.7 | 8.7 | | | | | | | | | | |
| Water | 12.4 | 14.7 | 8.7 | 15 | 15 | 15 | 15 | 12 | 4.0 | 3.8 | 5.0 | | 12.4 |
| HEMA | 81.4 | 54.8 | 72 | 72.7 | 73 | | 58 | 35.2 | 38.2 | 38.6 | 37.8 | 19.7 | 55 |
| TMPTMA | 3.0 | 2.1 | 2.5 | 2.5 | 2.2 | | 2.1 | 2.1 | 2.2 | 2.5 | 2.1 | | 2 |
| UDMA | | | | | 5.9 | | | | | | | 1.0 | |

TABLE 2-continued

| Component | 10* | 11 | 12 | 13 | 14 | 15 | 16 | 17 | 18 | 19 | 20 | 21* | 22** |
|---|---|---|---|---|---|---|---|---|---|---|---|---|---|
| Bis-GMA | | 12.0 | 7.0 | 5.9 | | | 6.0 | 9.1 | 9.6 | 10.6 | 9.8 | 64 | 12 |
| PMGDM | | | | | | | 5.5 | 13.7 | 16.2 | 14.8 | 14.6 | 4.6 | 5.5 |
| POSS | | | | | | | | | | | 1.0 | 1.5 | |
| Acetone | | | | | | | 9.8 | 24.3 | 26 | 26 | 26 | 8.2 | 9.8 |
| BHT | 0.01 | 0.02 | 0.02 | 0.05 | 0.05 | | | 0.02 | 0.02 | 0.02 | 0.02 | 0.02 | 0.02 |
| L-TPO | | | | | | | | | | | | | |
| CQ | 0.4 | | | | | | | | | | | 0.25 | 0.25 |
| EDMAB | 0.6 | | | | | | | | | | | 0.75 | 0.75 |
| Number of layers brushed on | 2 | 2 | 2 | 2 | 2 | 2 | 2 | 2 | 1 | 1 | 1 | 2 | 2 |
| Time for light cure of adhesive (seconds) | 20 | 20 | 20 | 20 | 20 | 20 | 20 | 20 | 10 | 10 | 10 | 10 | 10 |
| Dentin Bonding Strength, Mpa (S.D.) | 8.2 (3.5) | 15.6 (3.1) | 20.2 (2.5) | 17.5 (3.6) | 18.2 (4.0) | 16.2 (2.4) | 16.8 (3.6) | 19.5 (3.4) | 26.1 (2.8) | 23.5 (5.4) | 24.8 (4.1) | 5.2 (4.6) | 25.2 (3.9) |

*Comparative Examples
**Composition gelled within one week

As may be seen by reference to the above Table 2, self-etching, priming adhesive compositions provide excellent bond strength. As another comparative example, two coats of composition 10 were applied as an etchant primer, followed by one coat of composition 22 as an adhesive. After cure for 10 seconds, the dentinal bonding strength was 22.4, with an S.D. of 2.7. The one-part, one-application inventive examples can thus provide bonding comparable to a combination of a primer/etchant and an adhesive.

In addition, the shelf life of each of Examples 10–22 was monitored. It was discovered that the shelf life of the composition was shortened when a tertiary amine (ethyl 4-N,N-dimethylaminobenzoate, EDMAB) was present. Further it was surprisingly discovered that phosphine oxide based photoinitiators do not affect the shelf life of the compositions.

The foregoing description illustrates preferred embodiments of the invention. However, concepts employed may, based upon such description, be employed in other embodiments without departing from the scope of the invention. Accordingly, the following claims are intended to recite the invention broadly, as well as in the specific forms herein.

What is claimed is:

1. A dental adhesive composition, comprising
an copolymerizable component consisting of an olefinically unsaturated monomer having an —SO$_3$ functionality, a copolymerizable multi-functional (meth)acrylate adhesive, and optionally, 2-hydroxyethyl methacrylate; and
a curing system; wherein the dental adhesive composition is in the form of a one-part composition without a fluoride releasing compound.

2. The composition of claim 1, wherein the —SO$_3$ terminated monomer is 2-acrylamido-2-methyl-propanesulfonic acid, 2-sulfoethyl methacrylate, 2-sulfopropyl (meth)acrylate, 4-sulfo-butyl (meth)acrylate, 3-sulfobutyl (meth)acrylate, 3-bromo-2-sulfopropyl (meth)acrylate, 3-methoxy-1-sulfo-propyl (meth)acrylate, 1,1-dimethyl-2-sulfoethyl (meth)acrylamide, 3-sulfopropylmethacrylate, an ester of one of the foregoing acids, a salt of one of the foregoing acids, or a combination comprising at least one of the foregoing acids, esters, or salts.

3. The dental adhesive composition of claim 1, wherein the copolymerizable multi-functional (meth)acrylate adhesive is a difunctional water dispersible ethoxylated Bisphenol A di(meth)acrylate, ethoxylated tetrabromo bisphenol A diacrylate, polyethylene glycol di(meth)acrylate, metallic di(meth)acrylate, highly propoxylated glyceryl tri(meth) acrylate, trifunctional monomer of pentaerythritol tri(meth) acrylate, tetrafunctional monomer of pentaerythritol tetra (meth)acrylate, pentafunctional monomer of pentaerythritol penta(meth)acrylate, pentaerythritol dimethacrylate, dipentaerythritol penta(meth)acrylate, trimethylolpropane tri (meth)acrylate, ethoxylated trimethylolpropane tri(meth) acrylate, di-trimethylolpropane tetraacrylate, tris(2-hydroxyethyl) isocyanurate, glycerol di(meth)acrylate, triethylene glycol dimethacrylate, the diglycidyl (meth)acrylate adduct of Bisphenol A, urethane dimethacrylate, or a combination comprising of one or more of the foregoing adhesives.

4. The composition of claim 1, wherein the copolymerizable multi-functional (meth)acrylate adhesive is glycerol di(meth)acrylate, trimethylolpropane di(meth)acrylate, triethylene glycol dimethacrylate, pentaerythritol tri(meth) acrylate, trimethylolpropane trimethacrylate, the diglycidyl methacrylate adduct of Bisphenol A, dipentaerythritol pentaacrylate, pentaerythritol dimethacrylate, urethane dimethacrylate, or a combination comprising at least one of the foregoing adhesives.

5. The composition of claim 1, wherein the curing system comprises a phosphine oxide photoinitiator.

6. The composition of claim 1, wherein the curing system consists essentially of a phosphine oxide photoinitiator.

7. The composition of claim 1, further comprising a solvent system.

8. The composition of claim 1, comprising 2-hydroxyethyl methacrylate.

9. A dental adhesive composition, comprising in intimate mixture
a copolymerizable component consisting of an olefinically unsaturated monomer having an —SO$_3$ functionality, a copolymerizable multi-functional (meth)acrylate adhesive, a carboxyl group-containing copolymerizable adhesion promoter different from the olefinically unsaturated monomer having an —SO$_3$ functionality and the copolymerizable multi-functional (meth)acrylate adhesive, and optionally, 2-hydroxyethyl methacrylate;

a solvent system; and a photoinitiator; wherein the dental adhesive composition is in the form of a one-part composition without a fluoride releasing compound.

10. The dental adhesive composition of claim 9, wherein the olefinically unsaturated monomer having an —SO$_3$ functionality is 2-acrylamido-2-methyl-propanesulfonic acid, 2-sulfoethyl methacrylate, 2-sulfopropyl (meth)acrylate, 4-sulfo-butyl (meth)acrylate, 3-sulfobutyl (meth)acrylate, 3-bromo-2-sulfopropyl (meth)acrylate, 3-methoxy-1-sulfo-propyl (meth)acrylate, 1,1-dimethyl-2-sulfoethyl (meth)acrylamide, 3-sulfopropylmethacrylate, an ester of one of the foregoing acids, a salt of one of the foregoing acids, or a combination comprising at least one of the foregoing acids, esters, or salts; the copolymerizable multi-functional (meth)acrylate adhesive is glyceryl di(meth)acrylate, trimethylolpropane di(meth)acrylate, triethylene glycol dimethacrylate, pentaerythritol tri(meth)acrylate, trimethylolpropane trimethacrylate, the diglycidyl methacrylate adduct of Bisphenol A, dipentaerythritol pentaacrylate, pentaerythritol dimethacrylate, urethane dimethacrylate, or a combination comprising at least one of the foregoing adhesives; and the solvent system comprises 2-hydroxyethyl acrylate.

11. A dental restoration comprising the cured composition of claim 1.

12. A dental restoration comprising the cured composition of claim 9.

13. A method of treating a tooth surface to increase adhesiveness of the surface, consisting essentially of:
etching, priming, and applying the dental adhesive to the tooth surface by applying the dental adhesive composition of claim 1 to the tooth surface; and
curing the composition.

14. The method of claim 13, wherein the curing is by exposure to actinic radiation.

15. The method of claim 13, further comprising applying a dental restorative material to the dental adhesive composition after cure of the dental adhesive composition.

16. The method of claim 13, further comprising applying a dental restorative material to the dental adhesive composition before cure of the dental adhesive composition.

17. A dental restoration made by the method of claim 13.

18. A method of making a dental restoration, consisting essentially of
applying the dental adhesive composition of claim 1 to tooth surface;
applying a dental restorative composition to the adhesive composition; and
curing the adhesive composition before or after applying the dental restorative composition.

19. The dental adhesive composition of claim 9, wherein the carboxyl group-containing adhesion promoter is N-tolyglycine-N-glycerol methacrylate, pyromellitic acid dimethacrylate, butane tetracarboxylic acid-bis-hydroxyethylmethacrylate, methacrylic acid, maleic acid, p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid, an anhydride of 4-methacryloyloxyethyltrimellitic acid, 4-(2-hydroxy-3-methacryloyloxy) butyltrimellitic acid, an anhydride of 4-(2-hydroxy-3-methacryloyloxy) butyltrimellitic acid, 2,3-bis(3,4-dicarboxybenzoyloxy)propyl methacrylate, methacryloyloxytyrosine, N-methacryloyloxyphenylalanine, methacryloyl-p-aminobenzoic acid, an adduct of 2-hydroxyethyl methacrylate with pyromellitic dianhydride, an adduct of 2-hydroxyethyl methacrylate with 3,3', 4,4'-benzophenonetetracarboxylic dianhydride, an adduct of 2-hydroxyethyl methacrylate with 3,3',4,4'-biphenyltetracarboxylic dianhydride, the reaction product of an aromatic dianhydride with an excess of 2-hydroxyethyl methacrylate, the reaction product of 2-hydroxyethyl methacrylate with ethylene glycol bistrimellitate dianhydride, the reaction product of 3,3',4,4'-diphenylsulfone tetracarboxylic dianhydride and 2-HEMA, the adduct of pyromellitic dianhydride with glycerol dimethacrylate, or a combination comprising at least one of the foregoing adhesion promoters.

20. A method of treating a tooth surface to increase adhesiveness of the surface, consisting essentially of:
etching, priming, and applying a dental adhesive to the tooth surface by applying the dental adhesive composition of claim 9 to the tooth surface; and
curing the composition.

* * * * *